US008815162B2

(12) United States Patent
Vossenaar et al.

(10) Patent No.: US 8,815,162 B2
(45) Date of Patent: Aug. 26, 2014

(54) MICROELECTRONIC SENSOR DEVICE FOR DNA DETECTION

(75) Inventors: Erik Robbert Vossenaar, De Meern (NL); Marc Wilhelmus Gijsbert Ponjee, Tilburg (NL); Hendrik Roelof Stapert, Eindhoven (NL); Mark Thomas Johnson, Velhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1341 days.

(21) Appl. No.: 12/303,448

(22) PCT Filed: May 24, 2007

(86) PCT No.: PCT/IB2007/051960
§ 371 (c)(1),
(2), (4) Date: Dec. 4, 2008

(87) PCT Pub. No.: WO2007/141700
PCT Pub. Date: Dec. 13, 2007

(65) Prior Publication Data
US 2009/0325164 A1    Dec. 31, 2009

(30) Foreign Application Priority Data

Jun. 8, 2006    (EP) ..................................... 06115176

(51) Int. Cl.
*G05D 23/00*    (2006.01)
(52) U.S. Cl.
USPC .......... 422/109; 422/108; 422/105; 422/82.12
(58) Field of Classification Search
CPC ............................................. B01L 2300/1822
USPC ................................ 422/109, 108, 105, 82.12
See application file for complete search history.

(56) References Cited

U.S. PATENT DOCUMENTS

| 6,864,140 | B2 | 3/2005 | Bryant |
| 6,867,048 | B2 | 3/2005 | Kovacs |
| 2002/0055119 | A1* | 5/2002 | Yasuda et al. ..................... 435/6 |
| 2004/0053254 | A1* | 3/2004 | Wangh et al. ..................... 435/6 |
| 2004/0151629 | A1 | 8/2004 | Pease et al. |
| 2005/0009070 | A1 | 1/2005 | Arciniegas et al. |
| 2005/0089891 | A1 | 4/2005 | Lin et al. |

FOREIGN PATENT DOCUMENTS

| WO | 0202794 A2 | 1/2002 |
| WO | 2005107938 A2 | 11/2005 |
| WO | 2006084457 A1 | 8/2006 |
| WO | 2007107947 A1 | 9/2007 |

* cited by examiner

*Primary Examiner* — Natalia Levkovich

(57) ABSTRACT

The invention relates to a microelectronic sensor device and a method for the investigation of biological target substances (20), for example oligonucleotides like DNA fragments. In one embodiment, the device comprises a reaction surface (RS) to which target specific reactants (10) are attached and which lies between a sample chamber (SC) and an array of selectively controllable heating elements (HE). The temperature profile in the sample chamber (SC) can be controlled as desired to provide for example conditions for a PCR and/or for a controlled melting of hybridizations. The reactant (10) and/or the target substance (20) comprises a label (12) with an observable property, like fluorescence, that changes if the target substance (20) is bound to the reactant (10), said property being detected by an array of sensor elements, for example photosensors (SE). The fluorescence of the label (12) may preferably be transferred by FRET to a different fluorescent label (22) or quenched if the target substance (20) is bound.

23 Claims, 2 Drawing Sheets

MICROELECTRONIC SENSOR DEVICE FOR DNA DETECTION

The invention relates to a microelectronic sensor device for the investigation of at least one biological target substance, particularly a nucleic acid molecule or fragment thereof, comprising the use of target specific reactants and a sensor component. The invention further comprises a method for the investigation of at least one biological target substance and a use of the microelectronic sensor device.

US 2005/0009070 A1 discloses a miniaturized biosensor comprising a multi-well plate, wherein the temperature in the reaction wells of said plate can be selectively controlled to provide optimal conditions for a Polymerase Chain Reaction (PCR). In U.S. Pat. No. 6,864,140 B2, a microsensor is described with local heating elements in the form of a thin film transistor formed on polycrystalline silicon on a substrate adjacent to a sample chamber where (bio-)chemical reactions take place. A further investigation of the sample in the sample chamber is however not possible with this known device. Moreover, U.S. Pat. No. 6,867,048 B2 discloses a microelectronic biosensor in which a microchip with an array of sensor elements is disposed on a membrane with heating elements. The membrane allows to control the temperature in an adjacent sample chamber in the same way for all sensor elements.

Based on this situation, it was an object of the present invention to provide means for a more accurate and cost-effective investigation of biological target substances, particularly in connection with PCR processes.

This objective is achieved by a microelectronic sensor device according to claim 1, and a use according to claim 22. Preferred embodiments are disclosed in the dependent claims.

A microelectronic sensor device according to the present invention is intended for the investigation of at least one biological target substance, for example DNA fragments. The term "investigation" shall comprise here the qualitative and/or quantitative detection of certain properties of the target substance and optionally also a processing of said substance, for example by PCR. The sensor device comprises the following components:
 a) A sample chamber in which the sample to be investigated can be provided. The sample chamber is typically an empty cavity or a cavity filled with some substance like a gel that may absorb a sample substance; it may be an open cavity, a closed cavity, or a cavity connected to other cavities by fluid connection channels. The sample chamber further contains at least one target specific reactant, said reactant and/or the target substance comprising a label that changes an observable property if the reactant reacts with the target substance (the change may take place during and/or after the reaction and may comprise the appearance or disappearance of the property). The reactant may for example comprise a probe molecule that specifically binds to certain biological target molecules, and the label may be a functional moiety of the reactant with some readily detectable property, e.g. fluorescence. The sample chamber may initially contain the reactant in solid (dried) form, which is then dissolved upon addition of a sample.
 b) A sensor component for detecting the mentioned observable property of the label. The sensor component may comprise a single sensor unit, optionally provided with a scanning unit for scanning different locations in the sample chamber sequentially. Alternatively, the sensor component may comprise a plurality of single sensor units that are associated with different locations in the sample chamber.
 c) A heating component for exchanging heat with at least a sub-region of the sample chamber when being driven with e.g. electrical energy. The heating component may preferably convert electrical energy into heat that is transported into the sample chamber. It is however also possible that the heating component absorbs heat from the sample chamber and transfers it to somewhere else under consumption of energy.
 d) A control unit for selectively driving the heating component (i.e. for supplying energy to it).

The described microelectronic sensor device allows to monitor the progress of a reaction between the target specific reactants in the sample chamber and a biological target substance contained in a sample by sensing the observable property of the label. Sensing said property before the reaction starts further allows to determine the amount of reactants or target substance in the sample chamber. Moreover, the heating component can be used to provide optimal conditions for the manipulation of e.g. a sensitive biological sample, or for testing the selectivity of the binding process.

According to a preferred embodiment of the microelectronic sensor device, the heating component comprises a heating array with a plurality of individually controllable heating elements. In the most general sense, the term "array" shall in the context of the present invention denote an arbitrary one-, two- or three-dimensional arrangement of a plurality of elements (e.g. the heating elements). Typically, such an array is two-dimensional and preferably also planar, and the (heating) elements are arranged in a regular pattern, for example a grid or matrix pattern. A heating array with selectively controlled heating elements can be used to generate practically any desired spatial and/or temporal temperature profile in the sample chamber.

In another preferred embodiment, the sample chamber comprises a reaction surface forming at least a part of its walls, wherein said reaction surface is covered with the at least one target specific reactant. Binding a target specific reactant to a surface has the advantage that it is immobilized at a defined location and in a defined concentration for optimal access by the sensor component. Moreover, the availability of spatial information allows that different capture probes can be present in the same reaction compartment. Additional, non-immobilized target specific reactants may or may not optionally be present in the residual sample chamber. An advantage of non-immobilized reactants is faster kinetics and better defined hybridizations (no influence of surface attachment).

According to still another preferred embodiment of the microelectronic sensor device, the control unit is adapted to drive the heating component such that an amplification process can take place in the sample chamber. The amplification may for example be a PCR process, which is an important tool for the amplification and investigation of nucleotide sequences and which requires control of temperature and repeated heating cycles. This can advantageously be provided by the heating component of the microelectronic sensor device. The PCR preferably takes place in solution to ensure efficient reaction kinetics and well-defined hybridization interactions of primers and/or detection probes with the analyte. Alternatively, surface-attached primers, surface-attached ampifluor primers, surface-attached LuX-primers, or surface-attached Scorpions may be used. The advantage of the latter approach is that multiple reactions can be present in the same reaction compartment, because spatial information is available. In theory, this could lead to higher sensitivities, because each reaction compartment is bigger and can therefore contain more sample volume.

The control unit may further be adapted to drive the heating component according to the melting curve of a hybridization between the reactant(s) and the associated target substance(s). The melting curve describes the breaking of the hybridization between target substance and reactant in dependence on the temperature. By increasing the temperature slowly along the melting curve, the hybridizations between weakly bound target substance and reactant are dissolved first, leaving finally only the strongest bindings of perfect matches between target substance and reactant. The melting temperatures of these duplexes are preferably designed to occur at a well-defined temperature or range of temperatures indicative of the sequence structure of the reactant. Thus, a stringency/specificity test of the hybridization can be carried out.

While the microelectronic sensor device may in principle comprise only one kind of target specific reactant, more versatile "multiplexed" investigations become possible if different kinds of target specific reactants are used. In a particular embodiment, these target specific reactants may be distributed on a reaction surface that is a part of the sample chamber. Moreover, said distribution may preferably be in alignment with a heating array of heating elements, as it was defined above. Thus, each region on the reaction surface that is associated with a particular heating element (i.e. the temperature in said region is predominantly controlled by said heating element) may be coated with an associated type of reactant. In general, the term "alignment" shall denote a fixed (translation-invariant) relation between the positions of two entities, i.e. the heating elements of the heating array and the differently coated regions on the reaction surface, in this case.

The sample chamber (and, if applicable, the reaction surface) may optionally comprise reaction compartments that are by definition physically separated from each other, for example by intermediate walls. In this way it is possible to perform, with a sample provided to the sample chamber, simultaneously a plurality of different processes in different reaction compartments.

The aforementioned reaction compartments are preferably in alignment with a heating array of heating elements, as it was defined above. The temperature control provided by the heating elements is then uniquely associated with the compartments. Each reaction compartment may particularly be associated with just one or possibly a few different heating elements. Moreover, the walls of the compartments may optionally be designed to provide heat insulation between the compartments.

The sensor component of the microelectronic sensor device may particularly comprise an array of sensor elements, for example photosensors for detecting fluorescence light emitted by the label. With a plurality of sensor elements it is possible to monitor in parallel different regions on the reaction surface and thus a plurality of processes that are simultaneously taking place.

The aforementioned sensor elements are preferably in alignment with a heating array of heating elements, as it was defined above. The heating and sensor elements may for example be arranged in pairs, or each heating element may be associated with a group of several sensor elements (or vice versa). The alignment has the advantage that the heating and sensor elements interact similarly at different locations. Thus, uniform/periodic conditions are provided across the arrays. This technology allows to carry out also (multiple) chemistry steps.

The heating component (or its heating elements, if present) may particularly comprise a resistive strip, a thin film transistor (TFT), a transparent electrode, a Peltier element, a radio frequency heating electrode, or a radiative heating (IR) element. All these elements can convert electrical energy into heat, wherein the Peltier element can additionally absorb heat and thus provide a cooling function.

The microelectronic sensor device may optionally comprise a cooling unit, e.g. a Peltier element or a cooled mass, in thermal contact with the heating component and/or with the sample chamber. This allows lowering the temperature of the sample chamber if necessary. In combination with a heating component for the generation of heat, a cooling unit therefore enables complete control of temperature in both directions.

The microelectronic sensor device may further comprise at least one temperature sensor which makes it possible to monitor the temperature in the sample chamber. The temperature sensor(s) may preferably be integrated into the heating component. In a particular embodiment, the heating component comprises at least one heating element that is designed such that it can be operated as a temperature sensor, which allows to measure temperature without additional hardware.

In cases in which a temperature sensor is available, the control unit is preferably coupled to said temperature sensor and adapted to control the heating component in a closed loop according to a predetermined (temporal and/or spatial) temperature profile in the sample chamber. This allows to provide robustly optimal conditions for the manipulation of e.g. a sensitive biological sample.

The microelectronic sensor device may further comprise a micromechanical or electrical device, for example a pump or a valve, for controlling the flow of a fluid and/or the movement of particles in the sample chamber. Controlling the flow of a sample or of particles is very important for a versatile manipulation of samples in a microfluidic device. In a particular embodiment, at least one of the heating elements may be adapted to create flow in a fluid in the sample chamber by a thermo-capillary effect. Thus, its heating capability can be exploited for moving the sample.

An electrically isolating layer and/or a biocompatible layer may be disposed between the sample chamber and the heating and/or sensor array. Such a layer may for example consist of silicon dioxide $SiO_2$ or the photoresist SU8.

When realizing a microelectronic sensor device according to the present invention, a large area electronics (LAE) matrix approach, preferably an active matrix approach, may be used in order to contact the heating component (or the heating elements, if present) and/or the sensor component (or the sensor components, if present). The technique of LAE, and specifically the active matrix technology, using for example thin film transistors (TFTs) is applied for example in the production of flat panel displays such as LCDs, OLEDs and electrophoretic displays. A line-at-a-time addressing approach may optionally be used to address heating elements by the control unit.

The reaction surface may be the surface of a microchip that comprises the heating component and/or the sensor component. In a preferred embodiment, the reaction surface comprises a porous membrane which provides a large area for the attachment of reactants.

The mutual arrangement of the sample chamber, the heating array, and the sensor component can be arbitrary as long as the desired cooperation between these components is achieved. If the sample chamber comprises a reaction surface coated with reactants, this reaction surface preferably lies adjacent to the heating component. Thus the heat exchange between the heating component and the interior of the sample chamber takes place through the reaction surface, providing an optimal temperature control at said surface where the decisive reactions take place.

The invention further relates to a method for the investigation of at least one biological target substance, which method comprises the following steps:

a) Providing a sample chamber with at least one target specific reactant, wherein the target specific reactant and/or the target substance comprises a label that changes an observable property if the reactant reacts with the target substance.

b) Controlling the presence of a target specific reactant in the sample chamber, wherein the term "control" being meant to comprise a simple monitoring process and optionally also an active change of the amount of reactant in the sample chamber based on the monitoring results. In any case, "controlling" will include a determination or measurement of the target specific reactant in the sample chamber, for instance an impedimetric measurement of reactant bound to a reaction surface. Optionally, the measurement itself may influence a chemical reaction between reactant and a surface (e.g. to immobilize the reactant), for example, by increasing the temperature at the surface.

c) Reacting a target substance with the target specific reactants, wherein such reactions typically comprises a binding or hybridization between reactant and target substance.

d) Measuring the changed observable property of the label during and/or after step c), i.e. the reaction between target substance and reactant.

The method in its general form comprises the steps that can be executed with a microelectronic sensor device of the kind described above. Therefore, reference is made to the preceding description for more information on the details, advantages and improvements of that method.

In a preferred embodiment of the method, the target specific reactant comprises the label, and the presence of the target specific reactant in the sample chamber is controlled by measuring the observable property of said label.

The target specific reactant may optionally be attached to a reaction surface in the sample chamber, which provides spatial information and thus allows for a plurality of parallel measurements.

The method may particularly include a precise (preferably closed-loop) temperature control in the sample chamber (or, if applicable, at the reaction surface) according to desired spatial and/or temporal temperature profiles. This allows the processing of sensitive biological samples, selectivity stringency of surface binding (hybridization) processes, and a control over temperature sensitive chemical reactions.

According to another preferred embodiment of the method, a PCR process is executed in the sample chamber, particularly at a reaction surface thereof.

Furthermore, the temperature at the reaction surface mentioned above can optionally be increased after step c) according to the melting curve of a hybridization between target substance and reactant.

In the following, preferred embodiments of the invention will be described that apply both to the microelectronic sensor device and the method defined above.

In a first particular embodiment of the microelectronic sensor device and/or the method, the observable property of the label comprises luminescence (optical and electrical, such as fluorescence, phosphorescence, electroluminescence), magnetization, absorbance, colorimetry and/or reflectance. For fluorescence to be observed, excitation light must be provided, for example by a backlight in the microelectronic sensor device. Such excitation light may also be used to observe phosphorescence.

In a practically important embodiment of the microelectronic sensor device or the method, the observable property of the label is present (i.e. detectable) if the target specific reactant has not yet reacted with the target substance. This allows e.g. to check the proper distribution of labeled reactant on a reaction surface after the fabrication of a microelectronic sensor device.

In another embodiment of the sensor device and/or the method, fluorescence of the label(s) is quenched if the target specific reactant has reacted with the target substance. The observation of said fluorescence before the reaction takes place allows e.g. to check the amount of reactant on a reaction surface. During the progressing reaction between reactant and target specific substance, the fluorescence will then decrease due to the associated quenching of fluorescence. This provides an indirect measure of the amount of reacted target specific substance. The quenching of fluorescence can particularly be achieved if the reactant comprises the label and the target substance comprises a quencher as a functional group.

In another important embodiment of the invention, fluorescence of the label(s) is changed by fluorescence resonance energy transfer (FRET) from an excited label of one reaction partner (e.g. the target specific reactant) to a fluorescent label of the other reaction partner (e.g. the target substance) if the target specific reactant has reacted with the target substance. Thus, fluorescence of the reactant's label, which takes place at a first wavelength, is changed to fluorescence of the label of the target substance, which takes place at a second (different) wavelength, or vice versa. This allows to determine both the amount of not-yet-reacted reactant and reacted target substance (or vice versa). The direct observation of reacted target substance allows for instance to distinguish between actually bound target substance one is interested in and by-processes that diminish fluorescence of the reactant's labels.

The biological target substance and/or the target specific reactant may particularly comprise proteins and/or oligonucleotides, for example DNA, RNA, PNA (peptide nucleic acid), LNA (locked nucleic acid), ANA (arabinonucleic acid), and/or HNA (hexitol nucleic acid). Oligonucleotides are of high importance in a large variety of biological investigations. They may for example be prepared in a PCR process, which can advantageously be executed with a microelectronic sensor device according to the invention due to the possibility of a versatile temperature control.

In another embodiment of the invention, the reactant comprises a primer for a PCR process. If the primer is immobilized, i.e. bound to a reaction surface, a "solid state PCR" is possible.

In the aforementioned embodiment, the reactant may particularly be a Scorpion primer that comprises both a PCR primer and a hybridization probe. This embodiment will be described in more detail with reference to the Figures.

The invention further relates to the use of the microelectronic sensor device described above for molecular diagnostics, biological sample analysis, chemical sample analysis, food analysis, environmental analysis and/or forensic analysis.

These and other aspects of the invention will be apparent from and elucidated with reference to the embodiment(s) described hereinafter. These embodiments will be described by way of example with the help of the accompanying drawings in which:

FIG. 1 schematically shows a perspective view of a microelectronic sensor device with a heating array and fluorescent reactants according to the present invention;

Like reference numbers in the Figures refer to identical or similar components.

Polymerase Chain Reaction (PCR) is a common technique used for the amplification of specific gene elements from a complex mixture of DNA fragments. It can for instance be used for gene expression profiling, genetic analysis, such as SNP profiling, forensic analysis, or detection and identification of infectious agents. For such purposes, simultaneous analysis of a large number of DNA templates may be necessary. Performing and analyzing multiple PCRs is however a laborious and expensive task.

It is therefore desired to develop a reliable system that allows simultaneous performance and/or analysis of multiple PCRs. For e.g. the identification of infectious agents (e.g. microbes in body fluids or food products) with PCR, a species-specific sequence must be analyzed. One approach to do this is to amplify a DNA fragment with primers specific for each species that can be potentially present. This, however, is a very laborious (and expensive) approach, because each PCR has to be run separately (the number of PCRs that can run in the same reaction tube is limited). Another approach is to do a so-called broadband PCR. Certain genes are highly conserved between species (e.g. bacterial rRNA genes). When such genes are chosen as PCR targets, primers that are identical for a large number of species can be used for PCR amplification. For the identification of the microbes, post-PCR hybridization with species-specific probes can be performed. This implies that for each species a specific probe is immobilized on a solid surface in a microarray fashion. When a pool of broadband PCR products is allowed to hybridize with the array, only the PCR products that are complementary to the probe will bind.

In the following, different embodiments are described that enable simultaneous performance and/or analysis of multiple PCRs, using a reaction surface in the form of a microarray in a microelectronic sensor device.

Figure 1:
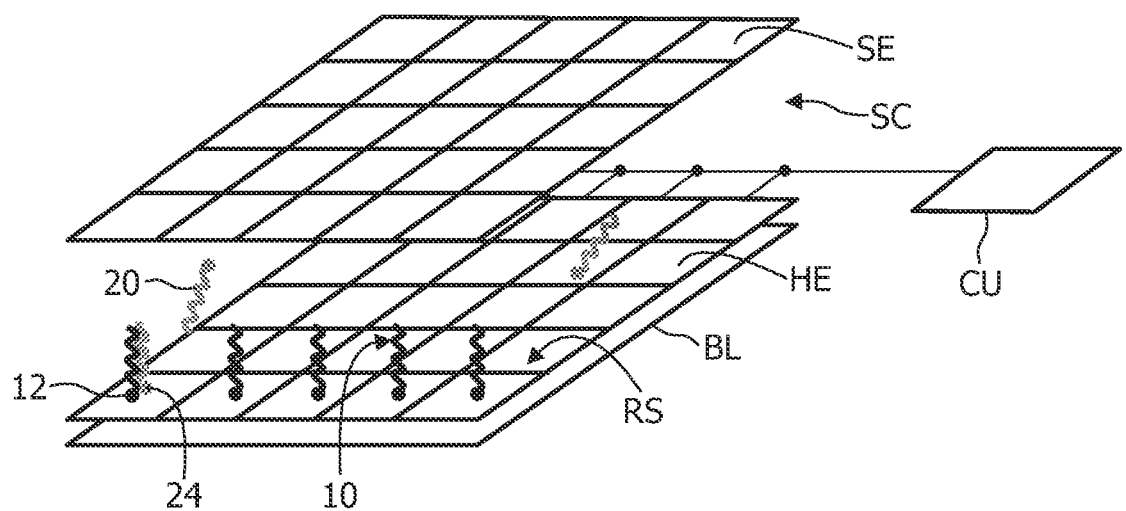

FIG. 1 shows schematically a typical design of a microelectronic sensor device according to the present invention. The device comprises a sample chamber SC in which a sample fluid comprising (biological) target molecules 20 can be provided. The bottom wall of the sample chamber SC is formed by a reaction surface RS on which target specific reactants 10 (i.e. hybridization probes in this example) are immobilized. The reaction surface RS may optionally be a porous material, which advantageously has a large area to which PCR products may bind. This improves the analysis speed, as the chance for hybridization of PCR products to the surface is enhanced, as well as the dynamic range of the procedure, since more probe molecules can be immobilized.

The reaction surface RS is arranged on top of a heating array consisting of a rectangular arrangement of heating elements HE that are coupled to a control unit CU for individual control. Thus, the spatial and temporal temperature profile in the sample chamber SC can be controlled as desired.

On top of the sample chamber SC, a sensor array is disposed consisting of a rectangular arrangement of individual sensor elements SE that are in alignment with the heating elements HE. The sensor elements SE can measure an observable property of labels 12 that are part of the reactants 10, wherein said property changes if the reaction between the reactant 10 and the corresponding target molecules 20 takes place.

In the embodiment shown in FIG. 1, the observable property of the labels 12 is fluorescence. The fluorescence of these labels is excited with a backlight BL arranged below the (transparent) heating array. To achieve a high excitation intensity, the backlight preferably comprises LEDs or lasers. Fluorescence light emitted by the labels 12 can be detected by the associated sensor elements SE in a spatially resolved way. If no target substance 20 is present, the measurement of fluorescence allows to verify the distribution and amount of reactants 10 immobilized on the reaction surface RS.

The labeled reactants 10 and target specific substances 20 are optionally designed such that the target substance comprises a quencher 24 that stops fluorescence of the labels 12 if the target substance is bound to the reactant. The resulting decline of fluorescence then provides a measure of the amount of bound target substance.

By including a discrete array of photosensors SE together with a discrete heating array, a fully integrated, "pixilated" system can be obtained. The array of photosensors may be based on CCD or CMOS technology and may in general be positioned below or above the reaction surface RS. Alternatively, the photosensors may comprise photodiodes or photo-TFTs (thin film transistors with transparent gate metal). In a preferred embodiment, the heating array and photosensor array are based on large area electronics technology and active matrix principles (e.g. low-temperature polysilicon—LTPS). An array based on active matrix principles may for example be incorporated as a component of the sensing device. Such a device is preferably manufactured by means of one of the well-known large-area electronics technologies, such as a-Si (amorphous silicon), LTPS or organic semiconductor technologies. A TFT, diode or MIM (metal-insulator-metal) could be used as an active element. The active matrix technology is commonly used in the field of flat panel displays for the drive of many display effects e.g. LCD, OLED and electrophoretic displays, and provides a cost-effective method of manufacturing a disposable biochemical module comprising e.g. a sensor array and a thermal processing array. In addition, the active matrix technologies allow cost-effective integration of components (e.g. temperature sensors, electrodes for electrical particle manipulation) other than those used for temperature control and optical sensing. This is advantageous, as biochips, or like systems, may contain a multiplicity of components, the number of which will only increase as the devices become more effective and more versatile.

The photosensors SE and heating elements HE are optionally positioned on top of the same substrate.

An advantage of an integrated array-form sensor device is the possibility to produce a fully integrated sealed PCR cartridge that only requires electrical external connections (increased robustness). This allows for portable applications, for instance a handheld read-out device. Moreover, complex and expensive optics in a read-out mother device are no longer needed, and rapid, real-time detection is possible; all areas within the sample chambers can be monitored continuously and simultaneously.

As hybridization of nucleic acid fragments products to probes is temperature-dependant, perfect hybridizations can be distinguished from single nucleotide mismatches at a critical temperature. Therefore, precise temperature control is essential in a hybridization microsensor. Specificity of binding can be determined by making a so-called melting curve.

Hybridization is performed at a lower than optimal temperature (sub-perfect matches are allowed). The temperature is then slowly increased while the fluorescence signal is constantly measured. Each mismatch will melt at a specific temperature until only the nucleic acid fragments that are perfectly complementary to the probe remain bound. This allows determination of specificity of binding.

The aforementioned procedure can particularly be performed with the microelectronic sensor device according to FIG. 1, which comprises an array-form temperature control. Each element of this device array is preferably coated with a different nucleic acid probe 10. A pool of nucleic acid fragments 20 can then be applied to the hybridization chamber SC and bind to the probe molecules 10. If the temperature of each element of the array is increased to the optimal temperature for each probe, unbound nucleic acid fragments may be washed away.

In a preferred embodiment, the heating array comprises a heating element HE (e.g. resistive heating element, TFT, Peltier, etc.) per element of the device array (i.e. uniquely coated region on the reaction surface). In addition, one or a plurality of temperature sensors (e.g. based on a change of resistance, p-n junction characteristics, TFT characteristics, thermocouple, etc.) may be integrated in the array. This sensor or these sensors may provide readout of the actual temperature. Furthermore, a closed feedback loop on the array may be used to control the temperature without the need for external controllers.

In another embodiment, pumping/mixing elements (e.g. electrodes) may be integrated in the temperature-controlled microelectronic sensor device for particle manipulation and/or to induce local convection, for instance based on electrokinetic principles (e.g. electrophoresis, electro-osmosis, dielectrophoresis, etc). This can advantageously enhance the binding kinetics of nucleic acid fragments to the reaction surface.

An advantage of the pixilated temperature control is therefore the possibility to do a precise melt curve analysis in a hybridization array format. This makes it possible to distinguish between specific and non-specific binding. Moreover, the optimum temperature can be individually adjusted for each probe, ensuring better assay kinetics and a faster hybridization. Finally, pixilated temperature control makes it possible to perform surface-attached ("solid state") multiplex PCRs, as described below with reference to FIG. 4.

Figure 2:
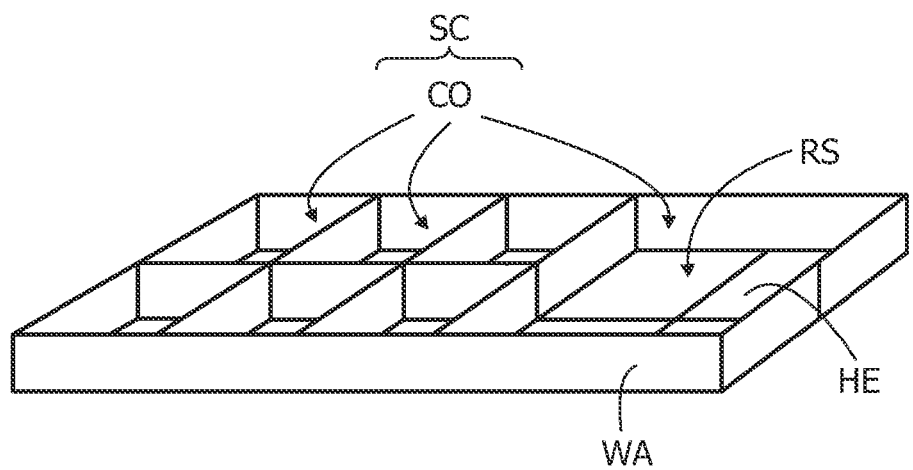
FIG. 2 shows the subdivision of a reaction surface into different compartments.

FIG. 2 illustrates a possible subdivision of the reaction surface RS into compartments CO that are separated by walls WA. The walls WA prevent uncontrolled mixing of sample fluid between the compartments. Depending on the requirements, the following embodiments are possible: (i) the entire sample chamber SC of the microsensor chip is constructed as a single chamber; (ii) each unit associated with one heating element/sensor element is constructed as a single chamber; or (iii) defined numbers of the aforementioned units are constructed as a single chamber. The use of different compartments in the chamber SC makes it possible to choose different PCR (buffer) conditions simultaneously on the same chip.

Figure 3A:
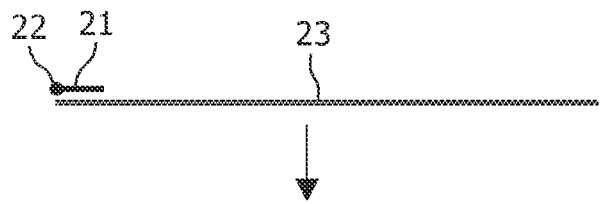
FIG. 3 is a diagram illustrating a measurement based on FRET.
Figure 3B:
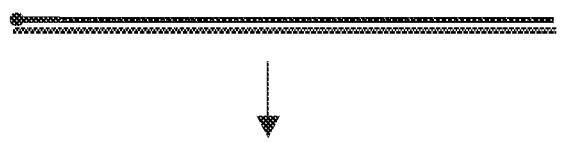
Figure 3C:
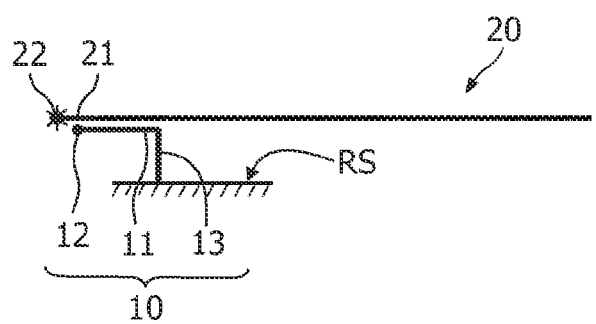

Coating of the reaction surface RS with target specific reactants (probe molecules) can for example be done using inkjet printing or lithographic technology. It is therefore desirable to be able to control the amount of material deposited in each spot of the reaction surface RS. As already mentioned, this can be achieved by attaching a fluorescent dye as a label to the probe molecules. Secondly, it is also desirable to be able to control for nonspecific binding (sticking) of labeled PCR products to the reaction surface. This can be achieved by taking advantage of the FRET (fluorescence resonance energy transfer) principle, which is illustrated in FIG. 3. The target specific reactant 10 consists in this case of a hybridization probe 11 attached via a link 13 to the reaction surface RS and carrying a fluorescent label 12.

The target substance 20 is prepared starting at stage A by PCR amplification with a primer 21 carrying a fluorescent label 22, which binds to a template strand 23. The resulting double-stranded DNA PCR product is then melted in stage B to free the amplified strand 20 which is the target substance of the detection process in stage C. Strand 20 can be amplified further by repeated PCR cycles or by repeated cycles of linear amplification. The strand 20 is able to hybridize with the probe molecule 11 bringing the two dye molecules 12 and 22 in close contact. By exciting the probe-attached dye molecule 12, the primer-attached dye molecule 22 is excited via FRET and emits detectable light. (Alternatively, FRET may be used the other way around, i.e. the fluorescent label 22 of the primer 21 is excited, and the probe-attached dye molecule 12 is detected. This will typically give less background, since fluorophores 22 are only present (and thus excitable) if the PCR product is present.)

Hence, the use of a labeled target-specific reactant 10 and a labeled primer 21, of which the latter can be excited by exciting the probe-attached dye molecule 12 via FRET, allows for both a control of the amount of probe molecules spotted on the reaction surface RS during the fabrication process and a strongly reduced detection of non-specifically bonded PCR products to the reaction surface.

In an additional embodiment, the labeled primer 21 may comprise a quencher instead of a dye molecule (22), so that upon (specific) binding of PCR products to the reaction surface, the fluorescence of the labeled probe 10 is quenched.

Figures 4A, 4B, 4C:
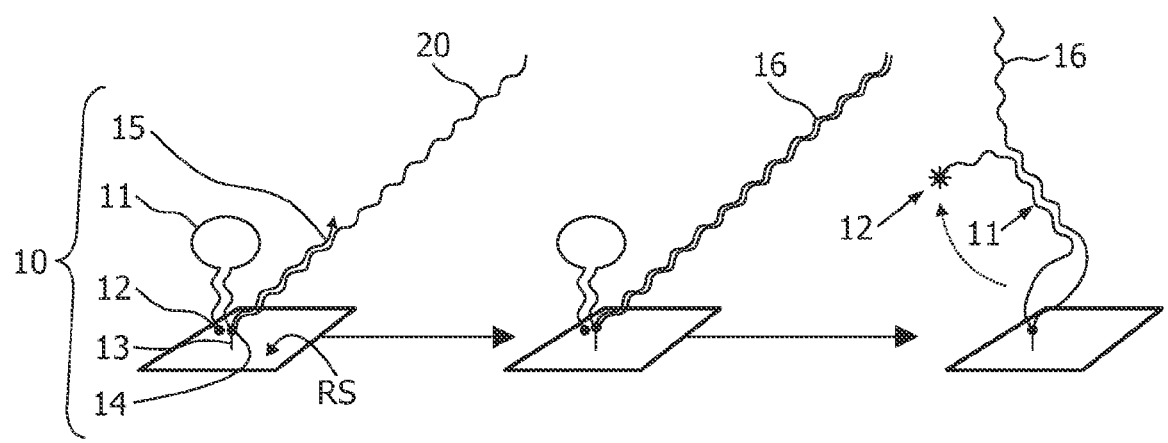
FIG. 4 is a diagram illustrating a measurement based on the use of a unimolecular Scorpion primer as reactant.

It was already mentioned that it is possible to do a "solid state" (surface-attached) PCR with a localized temperature control. Instead of attaching a probe oligonucleotide, one (or both) PCR primer(s) is (are) attached to a solid surface in this case. An example of this approach is illustrated in FIG. 4, wherein a Scorpion primer is attached to the reaction surface. This type of primer functions both as a PCR primer and a hybridization probe and is very suitable for fast real-time PCR detection with excellent discriminatory power (of single-base mismatches). A Scorpion consists of a specific probe sequence that is held in a hairpin loop conformation by complementary stem sequences on the 5' and 3' sides of the probe. A fluorophore 12 (serving as label) is attached to the 3'-end of the loop. The hairpin loop structure is linked to the 5'-end of a primer 15 via a PCR stopper 14. The PCR stopper functions as a quencher for the fluorophore 13. The scorpion is bound to a solid reaction surface RS via a linker moiety 13 that is attached to the PCR stopper 14.

In stage A, a template molecule 20 binds to the primer 15 and is elongated during PCR amplification. After the elongation has been completed (stage B), the template 20 is melted from the amplicon 16. When the temperature is lowered, the specific probe sequence 11 is able to bind its complement in the amplicon 16 (stage C). This hybridization opens up the hairpin loop so that fluorescence of label 12 is no longer quenched and a fluorescent signal can be measured. The PCR stopper 14 prevents read-through, which could lead to opening of the hairpin loop in the absence of the specific template. This thus prevents false signals from non-specific PCR products, such as primer dimers or mispriming events. The number of Scorpion primers attached to the reaction surface RS (e.g. average density×surface area) should at least exceed the number of fluorophores needed to cause a fluorescent signal larger than that of the threshold signal set for the real-time PCR analysis.

The advantages of the described scheme comprise:

The use of Scorpion primers brings double specificity to the system: both the primer sequence and the probe sequence must match in order to give a signal. Because primer and probe are combined in one molecule, Scorpion primers have shown superior performance to other real-time detection methods (e.g. Taqman probes or molecular beacons) under fast cycling conditions.

The small volume of PCR space above each pixel makes extremely fast cycling possible, which reduces the time needed for the entire assay. In addition, costs of biochemicals (primers, enzymes) are reduced.

Solid-state PCR can easily be combined with a pixilated detection sensor, creating an integrated PCR system.

Using different fluorophores or different locations on the surface allows for multiplexed detection (i.e. detection of different targets).

In the described embodiment (but also in other embodiments described in this disclosure), both primers can be sequence-specific, or one primer can be a broadband primer. Moreover, one of the primers can be surface-attached while the other primer can be soluble, or both primers can be surface-attached. In an additional embodiment, a mixture of forward (e.g. Scorpion) and reverse primers is deposited (e.g. by inkjet printing) on the reaction surface. This bypasses the need for compartmentalization of the PCR array as both the forward and the reverse strand of the PCR product remain attached to the surface. Non-compartmentalized PCR chambers are more simple to construct and will provide better sensitivity with samples containing very low template concentrations.

For all embodiments of the invention, the following additional statements apply:

The probe molecules 10 can comprise a DNA, RNA, PNA (peptide nucleic acid), LNA (locked nucleic acid), ANA (arabinonucleic acid), or HNA (hexitol nucleic acid) oligonucleotide.

RNA, PNA, LNA, and HNA are able to form heteroduplexes with DNA that are more stable that DNA:DNA homoduplexes. This ensures enhanced discrimination ability for sequence mismatches (more specific hybridization). The higher stability of heteroduplexes also allows the use of shorter oligonucleotide probes at a given temperature, reducing the chance of non-specific binding.

Formation PNA:DNA duplexes are formed independent of ionic strength of the hybridization buffer. This makes it possible to use low-salt buffers that prevent unwanted renaturation of dsDNA PCR amplicons.

While the embodiments have been exemplified mostly for microbial DNA identification, the methods are also applicable to other PCR multiplexing subjects, like genotyping, gene expression profiling, etc.

Moreover, the embodiments have been exemplified mostly with fluorescent detection. Evidently, other means of detection (magnetic, luminescence, absorbance, reflectance) are also feasible for some of the embodiments (with the exception of FRET-based detection).

In summary, the invention discloses the possibility to use several advanced features for microarray-type PCR detection:

FRET-based detection with the main advantages of being able to validate reaction surface production and enhanced specificity by reducing false-positive signals.

Localized temperature control with the main advantages of being able to enhance specificity by controlling the optimum hybridization temperature for each element of the array of the reaction surface and being able to do solid-state PCR.

Solid-state PCR with the main advantage of being able to do miniaturized real-time multiplex PCR in an integrated system.

An integrated pixilated detector with the main advantage of being able to make a fully integrated and robust PCR cartridge that does not require a read-out mother machine with sophisticated optics.

Finally, it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A microelectronic sensor device for the investigation of at least one biological target substance, comprising:
   a sample chamber containing at least one target specific reactant, wherein at least one of the target specific reactant and the biological target substance comprises a label that changes an observable property if the target specific reactant reacts with the biological target substance;
   a sensor component comprising an array of individual sensor elements for detecting the observable property of the label;
   a heating component for exchanging heat with at least a sub-region of the sample chamber;
   a control unit for selectively driving the heating component.

2. The microelectronic sensor device of claim 1, wherein the heating component comprises a heating array with a plurality of heating elements.

3. The microelectronic sensor device of claim 1, wherein the sample chamber comprises a reaction surface that is covered with the target specific reactant.

4. The microelectronic sensor device of claim 1, wherein the control unit is adapted to drive the heating component such that a PCR process can take place in the sample chamber.

5. The microelectronic sensor device of claim 1, wherein the control unit is adapted to drive the heating component according to the melting curve of a hybridization between the biological target substance and the target specific reactant.

6. The microelectronic sensor device of claim 2, wherein the at least one target specific reactant comprises a plurality of target specific reactants, and wherein the sample chamber comprises a reaction surface and wherein different kinds of the plurality of target specific reactants are distributed across the reaction surface in a pattern that is in alignment with the heating array.

7. The microelectronic sensor device of claim 1, wherein the sample chamber comprises a plurality of reaction compartments.

8. The microelectronic sensor device of claim 7, wherein the heating component comprises a heating array with a plurality of heating elements, and wherein the reaction compartments are in alignment with the heating elements.

9. The microelectronic sensor device of claim 2, wherein the heating component comprises a heating array with a plurality of heating elements, and wherein the sensor elements are in alignment with the heating elements.

10. The microelectronic sensor device of claim 1, wherein the heating component comprises at least one of a resistive strip, a thin film transistor TFT, a transparent electrode, a Peltier element, a radiofrequency heating electrode, and a radiative heating electrode.

11. The microelectronic sensor device of claim 1, further comprising at least one temperature sensor.

12. The microelectronic sensor device of claim 11, wherein the control unit is coupled to said at least one temperature sensor and adapted to control the heating component in a closed loop according to a predetermined temperature profile in the sample chamber.

13. The microelectronic sensor device of claim 1, further comprising one of a micromechanical device and an electrical device for controlling at least one of a flow of a fluid and a movement of particles in the sample chamber.

14. The microelectronic sensor device of claim 1, wherein a large area electronics matrix is used to contact at least one of the heating component and the sensor component.

15. The microelectronic sensor device of claim 3, wherein the reaction surface comprises a surface of a porous membrane.

16. The microelectronic sensor device of claim 3, wherein the reaction surface lies adjacent to the heating component.

17. The microelectronic sensor device of claim 1, wherein the observable property of the label comprises luminescence.

18. The microelectronic sensor device of claim 1, wherein the observable property of the label is present when the target specific reactant has not reacted with the biological target substance.

19. The microelectronic sensor device of claim 1, wherein fluorescence of the label is quenched when the target specific reactant has reacted with the biological target substance.

20. The microelectronic sensor device of claim 1, wherein fluorescence of the label is changed by fluorescence resonance energy transfer (FRET) to a fluorescent label of at least one of the biological target substance and the target specific reactant when the target specific reactant has reacted with the biological target substance.

21. The microelectronic sensor device of claim 1, wherein at least one of the biological target substance and the target specific reactant comprises at least one of a protein and an oligonucleotide.

22. The microelectronic sensor device of claim 1, wherein the target specific reactant comprises a primer for a PCR process.

23. The microelectronic sensor device of claim 1, wherein the target specific reactant is a scorpion primer comprising both a PCR primer and a hybridization probe.

* * * * *